US009284238B2

(12) United States Patent
Müller et al.

(10) Patent No.: US 9,284,238 B2
(45) Date of Patent: Mar. 15, 2016

(54) METHOD FOR PURIFICATION OF A HYDROCARBON STREAM CONTAINING OLEFIN AND AMINE

(75) Inventors: Wolfgang Müller, Munich (DE); Marco Harff, Munich (DE); Anton Wellenhofer, Munich (DE); Anina Wöhl, Munich (DE); Heinz Bölt, Munich (DE); Andreas Meiswinkel, Munich (DE)

(73) Assignees: SAUDI BASIC INDUSTRIES CORPORATION, Riyadh (SA); LINDE AG (DE)

( * ) Notice: Subject to any disclaimer, the term of this patent is extended or adjusted under 35 U.S.C. 154(b) by 289 days.

(21) Appl. No.: 13/988,776

(22) PCT Filed: Sep. 27, 2011

(86) PCT No.: PCT/EP2011/004828
§ 371 (c)(1),
(2), (4) Date: Jun. 27, 2013

(87) PCT Pub. No.: WO2012/069104
PCT Pub. Date: May 31, 2012

(65) Prior Publication Data
US 2013/0267752 A1   Oct. 10, 2013

(30) Foreign Application Priority Data
Nov. 23, 2010 (EP) .................................... 10192247

(51) Int. Cl.
C07C 7/04   (2006.01)
(52) U.S. Cl.
CPC ...................................... *C07C 7/04* (2013.01)

(58) Field of Classification Search
None
See application file for complete search history.

(56) References Cited

U.S. PATENT DOCUMENTS 5,811,619 A   9/1998   Commereuc et al.

FOREIGN PATENT DOCUMENTS

| CN | 1980873 A | 6/2007 |
| EP | 2258674 A1 | 12/2010 |
| WO | 2006048098 A1 | 5/2006 |
| WO | 2009095147 A1 | 8/2009 |
| WO | 2010127752 A1 | 11/2010 |

OTHER PUBLICATIONS

Extended European Search Report; European Application No. 10192247.4; Date of Mailing: Mar. 2, 2011; 5 Pages.
International Search Report; International Application No. PCT/EP2011/004828; International Filing Date: Sep. 27, 2011; Date of Mailing: Dec. 13, 2011; 3 Pages.
Chinese Patent No. 1980873; Date of Publication: Jun. 13, 2007; Abstract Only, 2 pages.

*Primary Examiner* — Tam M Nguyen
(74) *Attorney, Agent, or Firm* — Cantor Colburn LLP

(57) ABSTRACT

The present invention relates to a method for purification of a hydrocarbon stream containing linear alpha olefins, isomers thereof and at least one organic amine, the linear alpha olefins, isomers and the amine having boiling points under atmospheric pressure which differ by at most 5° C., comprising the step of removing a major amount of the organic amine from the hydrocarbon stream by distillation, wherein the distillation is carried out to that, together with the amine, between 5% and 95 wt % of the isomers, based on the total amount of the isomers in the hydrocarbon stream, are removed from the hydrocarbon stream in an amine/isomer-rich fraction.

20 Claims, No Drawings

METHOD FOR PURIFICATION OF A HYDROCARBON STREAM CONTAINING OLEFIN AND AMINE

CROSS REFERENCE TO RELATED APPLICATIONS

This application is a 371 of International Application No. PCT/EP2011/004828 filed Sep. 27, 2011, which claims priority to European Application No. 10192247.4, filed Nov. 23, 2010, both of which are hereby incorporated by reference in its entirety.

SPECIFICATION

The present invention relates to a method for purification of a hydrocarbon stream containing linear alpha olefins, isomers thereof and at least one organic amine.

In the chemical industry, processes are often conducted resulting in an outlet stream product or a feed stream to a process unit comprising hydrocarbons and amines. An example thereof is the outlet stream from a reactor utilized for preparing linear alpha-olefins by oligomerization of ethylene. The linear alpha-olefins produced are then separated into different fractions for further use or marketing. Often, an amine is added during the oligomerization process or is added into a reactor outlet piping system. Such processes are, for example, disclosed in U.S. Pat. No. 5,811,619 or WO 2009/095147. In other processes, amines are utilized as corrosion inhibitors or for adjustment of the pH value.

In many cases, it is difficult to remove the organic amine from the hydrocarbon stream or fractions thereof by distillation as the boiling points of the amine and the hydrocarbon stream, and especially fractions thereof, are very close. For example, n-dodecyl amine (DDA) is often added in an oligomerization process which after the product fractionation finally ends up in the $C_{14}$-LAO-product fraction. The same is true for the addition of 2-ethyl-hexyl-amine which has a very close boiling point to $C_{10}$-linear alpha olefins.

Due to the close boiling points of the amines, the linear alpha-olefins and its isomers, it was so far assumed that the amines cannot be removed by distillation.

Several prior art is available disclosing that a simple conventional distillation is excluded for separating mixtures of components having very close boiling points. Also azeotropic or extractive distillation, which are well known in the state of the art, cannot be utilized for these purposes, as no adequate azeotrope forming agent or extraction agent could be identified so far.

Thus, presently no commercially available method is known for the removal of an amine from a respective hydrocarbon stream. The comparably high concentration of the amine in the product stream complicates its removal.

As a consequence of this, in non-published European patent application 09 006 159.9, a method for removal of an organic amine from a hydrocarbon stream has been developed wherein the amine contained in the hydrocarbon stream is reacted with an acid and formed into an amine salt. Subsequently, the amine-salt formed can be extracted into an aqueous phase.

However, this method results in plants with considerable investment cost under utilization of acid-resistant materials of construction.

It was further found, that the hydrocarbon stream which is an outlet stream from a reactor for preparing linear alpha-olefins (LAO), or a fraction thereof, contains amongst linear alpha-olefins also isomers thereof, namely isomers having internal double bonds and/or branched isomers, which also have to be separated from the desired linear alpha-olefins to improve the purity of the LAO's.

Separating a hydrocarbon stream by reacting the organic amine with an acid, as disclosed in EP 09 006 159.9, would keep such isomers in the hydrocarbon stream so that the quality of the linear alpha-olefins, the desired main product, is not significantly improved.

It is therefore an object of the present invention to provide a method for purification of a hydrocarbon stream containing linear alpha-olefins, isomers thereof and at least one organic amine, which overcomes the drawbacks of the prior art. Especially, a method shall be provided which avoids the requirements of high investment costs and the use of acid-resistant materials of construction, as well as a method which also removes a significant amount of isomers from the desired linear alpha-olefin end product.

This object is achieved by a method for purification of a hydrocarbon stream containing linear alpha olefins, isomers thereof and at least one organic amine, the linear alpha olefins, isomers and the amine having boiling points under atmospheric pressure which differ by at most 5° C., comprising the step of removing a major amount of the organic amine from the hydrocarbon stream by distillation, wherein the distillation is carried out to that, together with the amine, between 5% and 95 wt % of the isomers, based on the total amount of the isomers in the hydrocarbon stream, are removed from the hydrocarbon stream in an amine/isomer-rich fraction.

The amine/isomer-rich fraction may be in the overhead product or the bottoms product of the distillation.

Preferably, the boiling points under atmospheric pressure of the linear alpha olefins, isomers thereof and the organic amine differ by at most 3° C., preferably 0.5-3° C.

As a minimum 5 wt % of the isomers shall be preferably removed together with the amine. Preferably approximately 80% of the isomers shall be removed together with the amine. More preferably approximately 95% of the isomers shall be removed together with the amine.

More preferred, the distillation is carried out under atmospheric pressure.

In one embodiment, a distillation column is utilized for removing the major amount of the organic amine, preferably having from 50 to 100 theoretical trays.

Even preferred, the hydrocarbon stream contains as major constituent linear $C_{10}$ alpha olefins and its isomers and/or linear $C_{14}$ alpha olefins and its isomers.

In one further preferred embodiment, the amine/isomer-rich fraction is further separated by removing the organic amine contained therein by converting with an acid and forming an amine salt, extracting the amine-salt formed into an aqueous phase, and optionally isolating the organic amine.

Further, separation of the organic amine is preferably in a batch or continuous operation.

Even preferred is that the amine/isomer-rich fraction is recycled to a reaction section of an oligomerization plant without prior separation.

Finally it is preferred that the isolated organic amine is recycled to a reaction section of an oligomerization plant.

Surprisingly, it was found that the inventive method for purification of a hydrocarbon stream containing linear alpha-olefins, isomers thereof and organic amine provides finally the possibility of significant removal of the amine and the isomers to improve the purity of the desired linear alpha-olefin products. Further, the inventive method avoids the requirement of acid-resistant materials of construction, as no acid for salt formation with the amine is necessary to be added.

For the present invention it is essential that by application of a conventional distillation step for removal of the amine simultaneously a certain portion of the isomers is removed together with the amine in the amine/isomer-rich fraction. As a result, the inventive method provides a hydrocarbon product of linear alpha-olefins which can be marketed without any restriction due to its amine content. Further, the inventive method allows easy and sufficient removal of the amine from the hydrocarbon stream. Additionally, the costs for the amine utilized in respective chemical reaction processes can be considerably reduced, since the amine can be recovered and recycled.

It is assumed that the isomers contained in the hydrocarbon stream may act as an (internal) extraction agent in the distillation step, resulting in an extractive distillation without the need to add a specific external extraction agent.

This is especially true for a method for preparing linear alpha-olefins, as disclosed above, wherein an organic amine is added into the oligomerization reactor and/or into a reactor outlet piping system.

Thus, in a most preferred embodiment of the invention, the method for purification is advantageously embedded in a method for preparing linear alpha-olefins (LAO) by oligomerization of ethylene, preferably in the presence of solvent and catalyst, comprising the steps of feeding ethylene into an oligomerization reactor, oligomerizing the ethylene in the reactor, removing a reactor outlet stream comprising linear alpha-olefins from the reactor via a reactor outlet piping system, optionally transferring the reactor outlet stream to a catalyst deactivation and removal step, and optionally deactivating and removing the catalyst from the reactor outlet stream, wherein at least one organic amine is added into the oligomerization reactor and/or into the reactor outlet piping system. The reactor outlet stream or a fraction thereof can then be taken as the hydrocarbon stream in the present invention.

In this regard, it is preferred that oligomerization is carried out in the presence of a catalyst comprising a zirconium component and an organoaluminium component, preferably a zirconium component having the formula $ZrCl_{4-m}X_m$, wherein X=OCOR or $OSO_3R'$ with R and R' being independently alkyl, alkene and phenyl, and wherein $0 \leq m \leq 4$, and wherein the organoaluminium compound is preferably $Al(C_2H_5)_3$, $Al_2Cl_3(C_2H_5)_3$, $AlCl(C_2H_5)_2$ or a mixture thereof.

The inventive method can be applied especially for LAO fractions which include respective amines. Amines can be, for example, n-dodecyl amine which is then usually obtained in the $C_{14}$-product fraction, and 2-ethyl-hexyl-amine which is usually obtained in the $C_{10}$ fraction of a fractionated crude LAO oligomerization product.

In a preferred embodiment, the amine contained in the amine/isomer-rich fraction can be removed there from by reaction with an acid in a continuous mode or in a batch operation and can then be recycled to the reaction section of a LAO plant.

Alternatively, the amine/isomer-rich fraction can be recycled to the reaction section of the LAO plant without prior separation for minimization of the requirements of a fresh amine. In order to avoid accumulation of isomers in the plant, a certain portion of that fraction has then preferably to be purged from the plant.

Additional features and advantages of the inventive method will now become apparent from the detailed description of a preferred embodiment.

An oligomerization of ethylene to result in linear alpha-olefins is carried out in a reactor utilizing a catalyst comprising a zirconium component and an organo aluminium component, a process which is well known in the art. Into the oligomerization reactor and/or into the reactor outlet piping system an organic amine is added, in the present example 2-ethyl-hexyl-amine.

After a first fractionation step of the LAO product from the oligomerization reactor a crude $C_{10}$ fraction is obtained comprising 1-decene as main product, organic amine and numerous decene isomers, such as internal and branched decenes. The crude $C_{10}$ fraction has the following composition (in weight percent):

| | |
|---|---|
| 1-decene | 90 |
| Amine | 3 |
| Decene isomers | 7 |

The crude $C_{10}$ fraction is then routed to a distillation column with 70 theoretical trays, operating at atmospheric pressure.

The distillation is operated at stable stationary conditions so that a certain portion of the $C_{10}$ isomers can be removed together with the amine in the overhead product, depending on the individual specification required for marketing of the $C_{10}$ product.

The distillation was carried out under atmospheric pressure for a specific time. Overhead product and bottoms product were then analyzed to result in the following purities:

| | Overhead product | Bottoms product |
|---|---|---|
| 1-decene | 22 | 97 |
| Amine | 25 | 1 wt ppm |
| Decene isomers | 53 | Balance |

(Figures generally given in wt-%. Figure for amine is 1 wt ppm)

Thus, it has been proven that the amine can be removed from the $C_{10}$ fraction to an adequate level, and, additionally, the purity of this product (bottoms product of the distillation) has been improved to 97 weight percent.

Analysis of overhead product and bottoms product is possible by means well known in the art, for example by gas chromatography. As is obvious for someone skilled in the art, analysis of the fractions can be carried out at the end of the distillation process, or can be done by taking samples of the fraction during distillation, for example on an online basis. Thus, the end of the distillation step can be fixed by the operator, i.e. when a desired amount of amine and/or isomers can be detected in the overhead product.

The features disclosed in the foregoing description and in the claims may, both separately and in any combination thereof, be material for realizing the invention in diverse forms thereof.

The invention claimed is:

1. A method for purification of a hydrocarbon stream containing linear alpha olefins, isomers thereof and at least one organic amine, comprising:

removing a major amount of the organic amine from the hydrocarbon stream by distillation;

wherein the distillation is carried out so that, together with the amine, between 5% and 95 wt % of the isomers, based on the total amount of the isomers in the hydrocarbon stream, are removed from the hydrocarbon stream in an amine/isomer-rich fraction of the distillation; and wherein the linear alpha olefins, isomers and the amine have boiling points under atmospheric pressure which differ by at most 5° C.

2. The method according to claim 1, wherein the boiling points under atmospheric pressure of the linear alpha olefins, isomers thereof and the organic amine differ by at most 3° C.

3. The method according to claim 1, wherein the distillation is carried out under atmospheric pressure.

4. The method of claim 1, wherein a distillation column is utilized for removing the major amount of the organic amine.

5. The method of claim 1, wherein the hydrocarbon stream contains as a major constituent linear $C_{10}$ alpha olefins and its isomers and/or linear $C_{14}$ alpha olefins and its isomers.

6. The method of claim 1, wherein the amine/isomer-rich fraction is further separated by removing the organic amine contained therein by converting with an acid, forming an amine salt, and extracting the amine-salt formed into an aqueous phase.

7. The method of claim 6, wherein further separation of the organic amine is in a batch or continuous operation.

8. The method of claim 1, wherein the amine/isomer-rich fraction is recycled to a reaction section of an oligomerization plant without prior separation.

9. The method of claim 6, further comprising isolating the organic amine.

10. The method of claim 9, wherein the isolated organic amine is recycled to a reaction section of an oligomerization plant.

11. The method of claim 2, wherein the boiling points differ by 0.5° C. to 3° C.

12. The method according to claim 2, wherein the distillation is carried out under atmospheric pressure.

13. The method of claim 4, wherein the distillation column has 50 to 100 theoretical trays.

14. The method of claim 1, wherein the amine is n-dodecyl amine.

15. The method of claim 1, wherein the amine is 2-ethyl-hexyl-amine.

16. The method of claim 1, wherein the purity of the linear alpha olefin after distillation is increased by greater than or equal to 5%.

17. A method for purification of a hydrocarbon stream containing linear alpha olefins, isomers thereof and at least one organic amine, comprising:
removing a major amount of the organic amine from the hydrocarbon stream by distillation, wherein the distillation is carried out so that, together with the amine, between 5% and 95 wt % of the isomers, based on the total amount of the isomers in the hydrocarbon stream, are removed from the hydrocarbon stream in an amine/isomer-rich fraction of the distillation;
removing the organic amine from the amine/isomer-rich fraction by converting with an acid, forming an amine salt, and extracting the amine-salt formed into an aqueous phase;
isolating the organic amine; and
recycling the organic amine to a reaction section of an oligomerization plant;
wherein the linear alpha olefins, isomers and the amine have boiling points under atmospheric pressure which differ by at most 3° C.

18. The method of claim 11, wherein the purity of the linear alpha olefin after distillation is increased by greater than or equal to 5%.

19. A method for purification of a hydrocarbon stream containing linear alpha olefins, isomers thereof and at least one organic amine, comprising:
removing a major amount of the organic amine from the hydrocarbon stream by distillation, wherein the distillation is carried out so that, together with the amine, between 5% and 95 wt % of the isomers, based on the total amount of the isomers in the hydrocarbon stream, are removed from the hydrocarbon stream in an amine/isomer-rich fraction of the distillation; and
recycling the amine/isomer-rich fraction to a reaction section of an oligomerization plant, without prior separation;
wherein the linear alpha olefins, isomers and the amine have boiling points under atmospheric pressure which differ by at most 3° C.

20. The method of claim 15, wherein the purity of the linear alpha olefin after distillation is increased by greater than or equal to 5%.

* * * * *